United States Patent [19]

Ackland et al.

[11] Patent Number: 5,300,428
[45] Date of Patent: Apr. 5, 1994

[54] ELECTROCHEMICAL DETECTION OF GROWTH OF MICRO-ORGANISMS

[75] Inventors: Martin R. Ackland; John K. Blundell, both of Wantage; William M. Hedges, Winchester; James F. Walpole, Oxfordshire, all of United Kingdom

[73] Assignee: CMB Packaging (UK) Limited, Worcester, United Kingdom

[21] Appl. No.: 905,220

[22] Filed: Jun. 29, 1992

Related U.S. Application Data

[63] Continuation of Ser. No. 520,442, May 8, 1990, abandoned.

[30] Foreign Application Priority Data

May 8, 1989 [GB] United Kingdom ............... 8910539
Sep. 18, 1989 [GB] United Kingdom ............... 8921068

[51] Int. Cl.⁵ .................. C12Q 1/04; C12Q 1/10; C12M 1/34; C12M 1/18
[52] U.S. Cl. ...................... 435/34; 435/38; 435/39; 435/291; 435/300
[58] Field of Search ............ 435/30, 39, 32, 289, 435/291, 34, 38, 300, 817; 422/67

[56] References Cited

U.S. PATENT DOCUMENTS

| | | | |
|---|---|---|---|
| 4,009,078 | 2/1977 | Wilkins et al. | 435/6 |
| 4,204,037 | 5/1980 | Dill et al. | 435/3 |
| 4,204,586 | 6/1980 | Nöller | 435/32 |
| 4,246,343 | 1/1981 | Wilkins et al. | 435/32 |
| 4,250,266 | 2/1981 | Wade | 435/289 |
| 4,288,544 | 9/1981 | Suzuki et al. | 435/39 |
| 4,321,322 | 3/1982 | Ahnell | 435/34 |
| 4,386,157 | 5/1983 | Nishioka et al. | 435/39 |
| 4,801,546 | 1/1989 | Ackland | 435/291 |

FOREIGN PATENT DOCUMENTS

| | | |
|---|---|---|
| 0036274 | 9/1981 | European Pat. Off. . |
| 1433887 | 4/1976 | United Kingdom . |
| 2000805 | 1/1979 | United Kingdom . |
| 2142433 | 1/1985 | United Kingdom . |
| 2177801A | 7/1986 | United Kingdom . |

OTHER PUBLICATIONS

Lehninger, A. in "Biochemistry" Worth Pub. Co. N.Y. (1976) Part 1: Chap. 13 pp. 339–341.
Gerhardt et al. in "Manual of Methods for General Bacteriology" Am. Soc. for Microb. W.D.C. p. 74 (1981).

Primary Examiner—Robert A. Wax
Assistant Examiner—Miguel H. Escallon
Attorney, Agent, or Firm—Burns, Doane, Swecker & Mathis

[57] ABSTRACT

A detection system for anaerobic micro-organisms involves the addition to a nutrient medium for the micro-organisms of an indicator species which is electrochemically reducible, soluble in the nutrient medium and consumed by the micro-organisms during growth. Two electrodes are immersed in the nutrient medium and changes in an electrical property of the nutrient medium are monitored. A preferred indicator species is riboflavin.

14 Claims, 2 Drawing Sheets

ELECTROCHEMICAL DETECTION OF GROWTH OF MICRO-ORGANISMS

This application is a continuation of application Ser. No. 07/520,442, filed May 8, 1990, now abandoned.

FIELD OF THE INVENTION

This invention relates to the electrochemical detection of growth of micro-organisms.

BACKGROUND TO THE INVENTION

Apparatus and methods are known for the detection of growth of micro-organisms using a sterile nutrient medium in which are placed two electrodes (anode and cathode). The growth of a micro-organism placed in the nutrient medium can be detected by measuring the changing potential between the electrodes. It has been observed that when growth of the micro-organisms reaches a particular stage the potential shows a marked change, e.g. a steep fall.

In our British Patent Specification No. 2142433 the applicants have described an apparatus by which the growth of micro-organisms in a plurality of samples can be monitored electrochemically, by monitoring the potential difference developed galvanically between two electrodes of different metals, e.g. gold and aluminium, in contact with the samples.

Further, in the applicants' British Patent Application Publication No. 2211615 there is described a method of detecting micro-organisms in a cell in which an electrical D.C. input is applied across the two electrodes while maintaining constant current or constant potential conditions in the cell, and monitoring either voltage or current respectively in the cell against time. While these and other similar systems have been used successfully for detection of micro-organisms, the underlying mechanism giving rise to monitorable electrical changes has not hitherto been fully understood.

It has been discovered by the present inventors that the underlying mechanism involves the reduction of free dissolved oxygen at the cathode in the transfer of electrical charge between the electrodes. Whilst for aerobic samples using gold and aluminium electrodes there is a measurable potential of the order of 400-500 mV in the absence of micro-organisms, falling to 200-300 mV with the growth of micro-organisms and consumption by them of the dissolved oxygen, for anaerobic cells the initial measurable potential is extremely low or even zero because of the absence of dissolved oxygen. With this condition it is on the face of it impossible to use the known electrochemical detection techniques for anaerobic organisms.

The present invention has been developed to enable the above-described electrochemical detection techniques to be used for anaerobic organisms.

SUMMARY OF THE INVENTION

According to one aspect of the present invention there is provided a method of detecting anaerobic growth of a micro-organism in a sterile nutrient medium, by sensing the change in one or more electrical properties of the nutrient medium between two electrodes in contact with the same, the method including forming a solution of the nutrient medium with an electrochemically reducible indicator species which is consumed by the micro-organism during anaerobic growth thereof.

The term "consumed" is used herein to denote a detectable alteration in the indicator species such that it can no longer be reduced at the relevant electrode.

A presently preferred indicator species is riboflavin. This has been found by the inventors to give start potentials which are comparable with existing aerobic detection systems and which remain steady until growth of micro-organisms reaches a particular level.

Using an aluminium (or aluminium alloy) anode the method preferably involves the addition to the nutrient medium of a phosphate buffer. This controls the PH of the medium and the dissolution of the aluminium of the anode, and so improves the signal-to-noise ratio of the system. Inorganic orthophosphates are suitable as the phosphate buffer.

From a second aspect thereof the invention also provides an apparatus for detecting anaerobic growth of a micro-organism. Accordingly such an apparatus comprises a nutrient medium in which has been dissolved an electrochemically reducible indicator species which is consumed by the micro-organism during anaerobic growth thereof, and, in contact with the nutrient medium, two electrodes with means for sensing, via said electrodes, a change in an electrical property of the nutrient medium during said anaerobic growth.

DESCRIPTION OF THE PREFERRED EMBODIMENT

For a better understanding of the present invention and to show how the same may be carried into effect, reference will now be made by way of example to the accompanying drawings in which:

BRIEF DESCRIPTION OF THE DRAWINGS

FIG. 1 shows a detection system formed by an electrochemical cell comprising a container 1 in which is placed a sterile nutrient broth 2. A gold electrode 3 and an aluminium electrode 4 secured in a stopper 5 are placed in contact with the nutrient medium 2. A further stopper 6 seals the container 1. A resistor 7 is connected across the electrodes 3,4 with a voltmeter 8 for sensing the potential galvanically developed across the resistor. The operation of the detection system of FIG. 1 for aerobic samples is known (for example, from our U.S. patent specification No. 4,801,546, issued on U.S. Ser. No. 06/709,035, filed Jun. 28, 1984 and assigned to the present applicants), and will not be described herein. However, to aid in understanding the present invention, an explanation of the mechanism underlying detection in aerobic samples will first be given.

The difference in absolute potentials between gold and aluminium electrodes in this system is of the order of 500 mV. Current generated by this electropotential is passed through the resistance 7. The current arises from electrons flowing from the aluminium electrode to the gold electrode since the aluminium electrode has a more negative potential. The present inventors have reasoned that, if when electrons arrive at the gold they are not removed, then the potential of the gold would quickly become more negative and ultimately reach that of the aluminium. The current would then cease. In the presence of dissolved molecular oxygen, however, this does not occur but instead oxygen molecules are reduced at the gold electrode by accepting electrons therefrom.

The source of electrons is maintained at the aluminium electrode by its slow dissolution as trivalently charged ions.

The reactions are probably:

At the Al electrode: $Al \rightarrow Al^{3+} + 3e-$

At the Au electrode: $O_2 + 2H_2O + 2e- \rightarrow H_2O_2 + 2OH^-$ and/or $O_2 + 2H_2O + 4e- \rightarrow 4OH$ In the absence of micro-organisms the oxygen in the medium 2 will result in a relatively large potential difference of about 400–500 mV, which may slowly decline as some of this oxygen is consumed at the cathode. However, as soon as organisms are introduced and begin to grow they start to consume the oxygen, the content of which in the medium is therefore reduced at an accelerated rate. Eventually the oxygen is substantially consumed, the potential difference between the two electrodes approaches zero, and current flow declines correspondingly. The potential difference across the electrodes is measured by the voltmeter 8, which accordingly provides a method of detecting the micro-organisms.

As the mechanism relies on the consumption of free oxygen, it is not suitable for anaerobic micro-organisms. By applying their discovery of the aerobic mechanism to anaerobic systems the present inventors have identified the necessary qualities of an indicator species which could be used in place of oxygen for an anaerobic system. The criteria which the Applicants believe must be satisfied are (1) that the indicator species should be electrochemically reducible;

(2) that it should be soluble in the nutrient medium; and (3) that it can be utilised by the micro-organisms for growth. It is also desirable that the indicator species should withstand autoclaving to sterilise the nutrient medium. This is not essential since other sterilising procedures, e.g. filtering, could be adopted. There is no obvious route to the isolation of suitable species satisfying these criteria, but the inventors have discovered that riboflavin is suitable, and is preferred.

Figure 1:
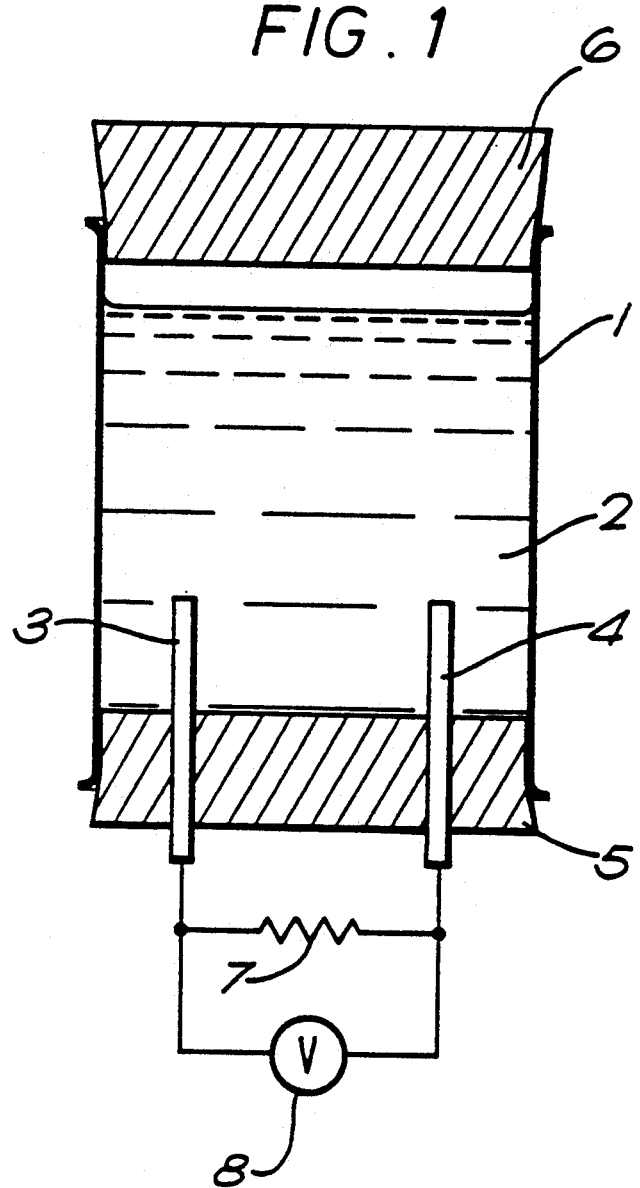
FIG. 1 is a diagrammatic sketch of an electrochemical detection apparatus.
Figure 2:
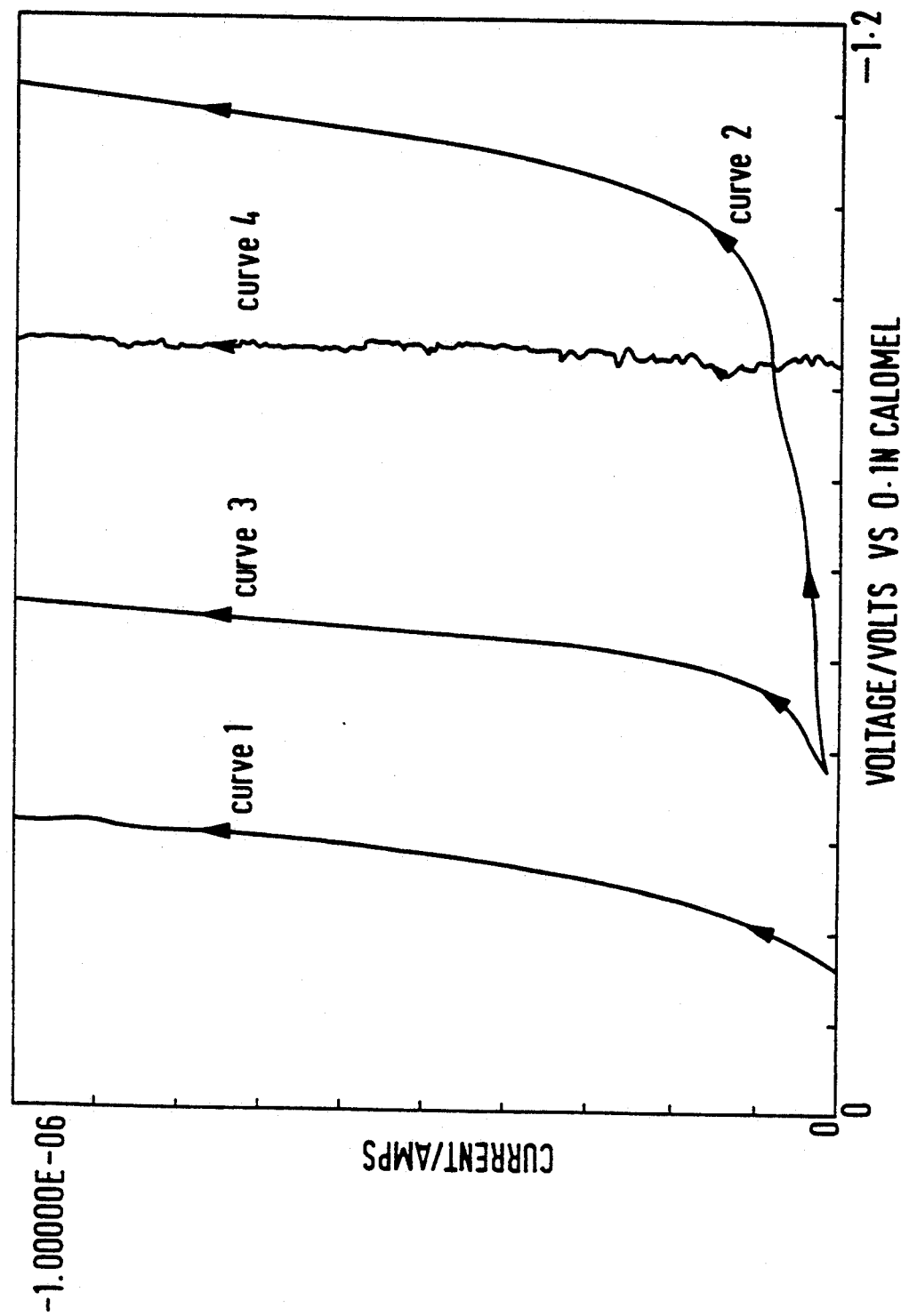
FIG. 2 is a graph comparing aerobic and anaerobic detection systems.

FIG. 2 compares the use of riboflavin in an anaerobic system with an aerobic system (in which oxygen is the indicator species).

FIG. 2, curve 1, shows the current/voltage curve for a fully aerated solution. The curve results from the reduction of oxygen and this is demonstrated by curve 2 which was obtained after de-oxygenating the same solution by bubbling nitrogen through it for about 2 hours. It is clear that under these conditions no current flows until much more negative potentials are reached, when the reduction of water occurs:

$2H_2O + 2e^- \rightarrow H_2 + 2OH^-$

However, when riboflavin is added to this anaerobic system, curve 3 is obtained indicating that the riboflavin is being electrochemically reduced.

Curve 4 shows the current/voltage curve for the dissolution of the aluminium electrode. (The modulus of the current has been taken since it has a positive sign because it is an oxidation reaction).

It is clear from these curves that the riboflavin behaves in a similar manner to oxygen and so should work in a detection system. However, because the curve for the riboflavin is closer to the aluminium curve than is the oxygen curve, a lower voltage would be expected when riboflavin is used in place of oxygen. It should also be noted that these experiments have been performed in salt solution, and some differences are to be expected when a micro-biological growth medium is used.

The applicants have introduced riboflavin into anaerobic control media, and have recorded steady voltages of about 350–400 mV. Moreover, when micro-organisms which have been introduced into the cells have grown, a significant reduction of this voltage to about 200 mV has occurred.

While the above description relates to an Al/Au electrode cell, it will be appreciated that similar results could be obtained in an impressed voltage or current system as is described in UK Patent Application Publication No. 2211615.

Further experiments have been carried out to isolate species other than riboflavin which are suitable for use in an anaerobic detection system.

An initial experiment involved screening 14 compounds that either had similar chemical structures to riboflavin or had structures which could accept electrons. Since the majority of the compounds expected to have a very small solubility in aqueous solutions, the following experimental protocol was used.

A control medium including the following constituents was prepared, using distilled water as solvent. The quantities given are per liter of distilled water.

| CONTROL MEDIUM | |
| --- | --- |
| Proteose Peptone No 3 | 10 g |
| Tryptone | 5 g |
| Yeast Extract | 5 g |
| D-Glucose | 2.5 g |
| Sodium Chloride | 2.3 g |
| Di-ammonium hydrogen orthophosphate | 7.3 g |
| Glutathione | 4 g |

After preparation the control medium was dispensed into containers and autoclaved for 15 minutes at 15 psi. Immediately after autoclaving the containers were stoppered.

1% w/v solutions/suspensions of the compounds to be tested were prepared in distilled water and 0.5 ml added to 50 ml of the control medium. The final concentration of each compound was a nominal 0.01%. Containers were then entered into an electrochemical detection system as follows, the experiments designated Lab Code 67-4 to 67-49 relating to the control medium with the addition of the compounds to be tested.

| LAB CODE | COMPOUND |
| --- | --- |
| 67-1 to 67-3 | Control, No Additions |
| 67-4 to 67-6 | Riboflavin (0.006%) |
| 67-7 to 67-9 | Nitrobenzene |
| 67-10 to 67-12 | 4-Nitrobenzaldehyde |
| 67-13 to 67-15 | 2-Nitroethanol |
| 67-16 to 67-18 | Nitrobenzoic Acid |
| 67-19 to 67-21 | p-Nitrophenylacetate |
| 67-22 to 67-24 | Folic Acid |
| 67-25 to 67-27 | 3-Nitro-L-Tyrosine |

-continued

| LAB CODE | COMPOUND |
|---|---|
| 67-28 to 67-30 | 2-Pyrazine Carboxylic Acid |
| 67-31 to 67-33 | 2,3 Dimethoxy-5-methyl 1,4 Benzoquinone |
| 67-34 to 67-36 | Menadione |
| 67-37 to 67-39 | Lumichrome--(i.e., 7,8-dimethylalloxazine)--, |
| 67-40 to 67-42 | Lumazine Monohydrate |
| 67-43 to 67-45 | Nicotinamide |
| 67-46 to 67-49 | P-Benzoquinone |

The applicants found that the control medium without any additions gave an unacceptably low signal. Moreover, the majority of the compounds listed above did not improve the signal level. However, two compounds, 4-Nitrobenzaldehyde and Lumichrome, when added to the control medium, resulted in a signal which was comparable to that given by the control medium with riboflavin. Therefore, Lumichrome, 4-Nitrobenzaldehyde and Naphthoquinone (which was not available for the initial screen but had previously been found to be effective) were examined further.

The same control medium as before was prepared, and the three compounds being studied further were added to amounts of this medium. The media produced were then sterilized either by autoclaving at 15 psi for 15 minutes or by filtration through a 0.22 μm membrane (with no precautions taken to keep the medium anaerobic). Immediately after sterilization the containers were stoppered and stored at room temperature for 24 hours. The containers were then entered into an electrochemical detection system as follows:

| LAB CODE | ADDITION |
|---|---|
| 69A and 69AF | Riboflavin (0.006%) |
| 69B and 69BF | Naphthoquinone (0.0015%) |
| 69C and 69CF | 4 Nitrobenzaldehyde (0.006%) |
| 69D and 69DF | Lumichrome (0.002%) |

(F denotes that the medium was filter sterilized).

It is to be noted that the solubility of the Napthoquinone and Lumichrome was such that even with the small amounts used, some of the compound failed to dissolve.

The containers were inoculated with either *Clostridium tetani* or *Bacteroides fragilis* on day 7 or *Clostridium perfringens* on day 8. Approximately 100 organisms were added to each bottle.

Initial "humps" appeared in the filter sterilized containers, probably the result of the presence of residual oxygen in the medium.

RIBOFLAVIN. The control containers gave the expected smooth signal of 400 mV and the growth of the test organisms was indicated by a voltage drop of 150 mV. Filter sterilized medium resulted in a signal of about 375 mV and *Cl. perfringens* failed to grow and thus to signal. Later experiments showed that some riboflavin derivatives, e.g. riboflavin phosphate, could be used instead of riboflavin.

NAPHTHOQUINONE. The voltage declined from 400 mV to 300 mV over the 10 day incubation period. Although growth of the three organisms was observed in this medium, the voltage drop was only 50 mV. In contrast medium that had been filter sterilized gave a voltage output of 500 mV. The signal from two of the bottles deteriorated after about day 5. Growth of *B. fragilis* was signalled by a voltage drop of 150 mV whilst *Cl. tetani* gave a 200-250 mV drop. *Cl. perfringens* failed to grow and thus to signal. A later experiment showed that 2-hydroxy-1, 4-naphthoquinone at 0.004% concentration could be used as the indicator species.

NITROBENZALDEHYDE. The voltage output from autoclaved medium was approximately 325 mV declining to 225 mV over the incubation period. Although growth of the test organisms was observed there was no voltage change. The signal response from filter sterilized medium was variable. All three test organisms grew with *B. fragilis* signalling after 24 hours and *Cl. tetani* after 48 hours. *Cl. perfringens* failed to signal, although the voltage output from this container was some 100 mV less than the other containers in the series.

LUMICHROME. The voltage output from autoclaved medium was less than 300 mV and the growth of the test organisms was not signalled by a voltage drop. Filter sterilized medium gave a high voltage output (c 500 mV) which declined over the ten day period. *Cl. tetani* failed to grow in this medium, whilst *B. fragilis* and a contaminant grew and signalled. (*Cl. perfringens* was not added to this series). The control container gave a response indicative of growth, but no contamination was visually observed.

In conclusion, filter sterilized media gave higher voltage outputs than media that had been autoclaved, suggesting that during autoclaving the compounds are either lost from the medium or changed in some way. However the signal generated by filtered media was generally less stable possibly because some residual oxygen was present. It is believed that this problem could be overcome by filter sterilizing and dispensing hot media in an anaerobic atmosphere, increasing the amount of reducing agent (e.g. glutathione) and/or increasing the equilibration time.

The present inventors have examined the effect of varying the phosphate buffer concentration in the control medium, by monitoring the signal generated by the control medium with 0.006% riboflavin. Reduction of the phosphate buffer concentration from 200 mM to 75 mM was shown to have little effect on signal quality, although the time taken to reach maximum voltage increased from 3 hours (200 mM buffer) to 12 hours (75 mM buffer). However, the experiments were performed in the absence of human blood. In the experiments set out below containing riboflavin as indicator species were prepared with five different potassium phosphate buffer concentrations, and 5 ml of human blood was added to the media on entry into an electrochemical detection system.

Solutions containing 125 mM potassium phosphate buffer and riboflavin at 0.006% concentration was diluted with the same basal medium but lacking any phosphate buffer to give a series of test media containing 0, 25, 50, 75, 100 and 125 mM buffer concentrations with 0.006% riboflavin. Regardless of buffer concentration, all the test media containing buffer had a pH of 7.3 after autoclaving whilst the corresponding pH value of the test medium without phosphate buffer was 7.8. Each test medium was dispensed into four containers, and the containers were autoclaved.

Human blood (5 ml) was added to the containers immediately on cooling, prior to their entry into the detection system. *Cl. tetani* was inoculated into one container from each test medium.

All the inoculated containers showed a response, the voltage signal level increasing with the phosphate buffer concentration. However, high levels of buffer concentration were found to delay the response, it is believed because of inhibition of the microbial growth by the phosphate. Low levels of buffer concentration, on the other hand, gave low signal-to-noise ratios.

Further studies carried out by the applicant have revealed or confirmed the following substances which can be used in place of riboflavin as the electrochemically reducible indicator species.

| | BATCH |
|---|---|
| RIBOFLAVIN TYPE COMPOUNDS | |
| Lumichrome | 90 |
| QUINONE TYPE COMPOUNDS | |
| Anthraflavic Acid | 93 |
| Anthraquinone-2,5-sulphonic Acid | 92 |
| Alizarin Red | 92 |
| (6 or 7 or 8 or 9)-Chloro-1,3-dimethylbenzo(G)-pteridine-2,4-(1H,3H)-dione | 92 |
| Fast Red Salt | 92 |
| 2-Hydroxy-1,4-Naphthoquinone | 90 |
| 1,4-Naphthoquinone | 94 |
| Purpurin | 94 |
| NITRO- TYPE COMPOUNDS | |
| 4-Nitrobenzyl Alcohol | 92,93 |
| 4-Nitrobenzaldehyde | 93 |
| m-Nitrobenzamidine | 93 |
| 4-Nitrobenzoyl-B-alanine | 94 |
| N(4-Nitrobenzoyl)-L-glutamic Acid | 92 |
| Nitrocinammaldehyde | 93 |
| OTHERS | |
| Reactive Blue 2 | 94 |
| Safranine | 94 |
| The following compounds gave a signal that was marginally better than the control. | |
| P-Nitrophenyl Phosphate | 93 |
| The following compounds gave a signal that was marginally better than the control and were not inoculated. | |
| 4-Nitrocatechol | 92 |
| 1,4-Diaminoanthraquinone | 92 |
| The following compounds are also regarded as being potential alternatives to riboflavin. | |
| Riboflavin Phosphate | |
| Nitrobenzene | |

What is claimed is:

1. A method for detecting anaerobic growth of a bacterial micro-organism in a sterile nutrient medium, wherein said bacterial micro-organism is capable of interaction with an indicator species as specified hereafter, said method consisting essentially of:
   (a) forming a solution of said nutrient medium and an indicator species selected from the group consisting of riboflavin, riboflavin phosphate, naphthoquinone, 2-hydroxy-1,4-naphthoquinone, nitrobenzaldehyde, and 7,8-dimethylalloxazine, with said indicator species being capable of accepting electrons from a cathode and of interacting with said bacterial micro-organism during anaerobic growth thereof so that the ability of the indicator species to accept electrons is altered in dependence on the growth of said bacterial micro-organism, and
   (b) sensing the change of one or more electrical properties of said solution while in direct contact with two electrodes, one of which is a cathode.

2. A method for detecting anaerobic growth of a bacterial micro-organism in a sterile nutrient medium according to claim 1 wherein said bacterial micro-organism is *Clostridium tetani*.

3. A method for detecting anerobic growth of a bacterial micro-organism in a sterile nutrient medium according to claim 1 wherein said bacterial micro-organism is *Clostridium perfringens*.

4. A method for detecting anaerobic growth of a bacterial micro-organism in a sterile nutrient medium according to claim 1 wherein said bacterial micro-organism is *Bacteroides fragilis*.

5. A method for detecting anaerobic growth of a bacterial micro-organism in a sterile nutrient medium according to claim 1 wherein said indicator species is riboflavin.

6. A method for detecting anaerobic growth of a bacterial micro-organism in a sterile nutrient medium according to claim 5 wherein said riboflavin is provided in said nutrient medium in a concentration of about 0.006 percent by weight.

7. A method for detecting anaerobic growth of a bacterial micro-organism in a sterile nutrient medium according to claim 1 wherein said indicator species is riboflavin phosphate.

8. A method for detecting anaerobic growth of a bacterial micro-organism in a sterile nutrient medium according to claim 1 wherein said indicator species is naphthoquinone.

9. A method for detecting anaerobic growth of a bacterial micro-organism according to claim 1 wherein said indicator species is 2-hydroxy-1,4-naphthoquinone.

10. A method for detecting anaerobic growth of a bacterial micro-organism according to claim 1 wherein said indicator species is nitrobenzaldehyde.

11. A method for detecting anaerobic growth of a bacterial micro-organism according to claim 1 wherein said indicator species is 7,8-dimethylalloxazine.

12. A method for detecting anaerobic growth of a bacterial micro-organism according to claim 1 wherein a phosphate buffer additionally is present in said solution of nutrient medium.

13. A method for detecting anaerobic growth of a bacterial micro-organism according to claim 12 wherein said phosphate buffer comprises potassium orthophosphate.

14. A method for detecting anaerobic growth of a bacterial micro-organism according to claim 1 whereon the other of said electrodes is an anode comprising aluminum.

* * * * *